United States Patent
Nakano

(10) Patent No.: US 8,192,483 B2
(45) Date of Patent: Jun. 5, 2012

(54) STENT TO BE PLACED IN THE LIVING BODY

(75) Inventor: Ryoji Nakano, Settsu (JP)

(73) Assignee: Kaneka Corporation, Osaka-shi (JP)

( * ) Notice: Subject to any disclaimer, the term of this patent is extended or adjusted under 35 U.S.C. 154(b) by 1056 days.

(21) Appl. No.: 12/089,363

(22) PCT Filed: Oct. 4, 2006

(86) PCT No.: PCT/JP2006/319891
§ 371 (c)(1),
(2), (4) Date: Apr. 4, 2008

(87) PCT Pub. No.: WO2007/040249
PCT Pub. Date: Apr. 12, 2007

(65) Prior Publication Data
US 2010/0131042 A1 May 27, 2010

(30) Foreign Application Priority Data

Oct. 6, 2005 (JP) .................................. 2005-293371

(51) Int. Cl.
*A61F 2/06* (2006.01)
(52) U.S. Cl. ...................................... 623/1.16; 623/1.15
(58) Field of Classification Search .................. 606/198, 606/194, 195, 191; 623/1.11, 1.12, 1.15, 623/1.16
See application file for complete search history.

(56) References Cited

U.S. PATENT DOCUMENTS

| | | | | |
|---|---|---|---|---|
| 5,868,783 A | * | 2/1999 | Tower | 606/198 |
| 6,027,526 A | * | 2/2000 | Limon et al. | 623/1.15 |
| 2002/0107560 A1 | | 8/2002 | Richter | 623/1.11 |
| 2004/0044400 A1 | * | 3/2004 | Cheng et al. | 623/1.16 |

FOREIGN PATENT DOCUMENTS

| | | |
|---|---|---|
| EP | 1 254 674 | 11/2002 |
| JP | 02-174859 | 7/1990 |
| JP | 06-009390 | 1/1994 |
| JP | 06-181993 | 7/1994 |
| JP | 2000-167065 | 6/2000 |
| WO | WO 91/12779 | 9/1991 |
| WO | WO 95/03036 | 2/1995 |
| WO | WO 02/065947 | 8/2002 |

\* cited by examiner

*Primary Examiner* — Tuan Nguyen
(74) *Attorney, Agent, or Firm* — Kratz, Quintos & Hanson, LLP

(57) ABSTRACT

It is intended to provide a stent to be placed in the living body which exhibits excellent extension properties even in a flexion site of a lumen in the body and shows a low restenosis rate after being placed in the living body. A stent to be placed in the living body characterized in that, as one of the characteristics thereof, the stent is in a long and thin tubular shape having both termini, the long and thin tubular body can be extended in the radial direction from the first diameter in the compressed state to the second diameter in the extended state, the stent has a first terminal section, a second terminal section, a third central section, a fourth section located between the first terminal section and the third central section and a fifth section located between the second terminal section and the third central section, the rigidity of the fourth section is lower than the rigidity of the first terminal section and lower than the rigidity of the third central section, and the rigidity of the fifth section is lower than the rigidity of the second terminal section and lower than the rigidity of the third central section.

12 Claims, 2 Drawing Sheets

31  34  33  35  32

41　　44　　　　43　　　　45　　42

51　　54　　　　53　　　　55　　52

61　　64　　　　63　　　　65　　62

STENT TO BE PLACED IN THE LIVING BODY

CROSS REFERENCE TO THE RELATED APPLICATIONS

This application is a national stage of international application No. PCT/JP2006/319891 filed on Oct. 4, 2006, which also claims benefit of priority under 35 U.S.C. §119 to Japanese Patent Application No. 2005-293371 filed on Oct. 6, 2005, the entire contents of which are incorporated herein by reference.

TECHNICAL FIELD

The present invention relates to a method of preventing and treating exuberant vascular proliferation and a medical stent for placement in body used for that purpose.

CROSS-REFERENCE TO RELATED APPLICATIONS

The disclosure in the description, claims, drawings, and abstract of Japanese Patent Application No. 2005-293371 (filed on Oct. 6, 2005) is hereby incorporated by reference in its entirety.

BACKGROUND ART

The stent is a medical device that is placed in blood vessel or other lumen in the body and that is used for dilation of its stricture or obstruction site and preservation of the lumen size and thus for treatment of various diseases caused by constriction or obstruction of blood vessel or other internal lumens. Examples of such stents include stents in the coiled shape of a single linear metal or polymeric material, those prepared by processing a metal tube with laser, assemblies of linear parts welded to each other with laser, those prepared by weaving multiple linear metal wires, and the like.

These stents are grouped into those expanded by balloon (balloon-expandable stents) and those expandable as they are when an external part restricting expansion is removed (self-expandable stents). Such a balloon-expandable stent is expanded and fixed to the lumen to be treated, as it is fixed to the balloon region of an intravascular catheter having an expandable part such as balloon at the distal end (balloon catheter) (in mounting step), the catheter fed to the site in the patient lumen to be treated, and the balloon expanded in the treatment site. Subsequently, the balloon is contracted, and the catheter withdrawn. In expanding the balloon, the expansion pressure is adjusted according to the condition of the lumen to be expanded and the mechanical strength of the stent used.

Demanded for such a stent are various properties such as strength sufficient for overcoming the pressure by the tubular organ to be expanded, flexibility allowing supply of the stent through a highly winding tubular organ to a desired site without problem, post-expansion flexibility preventing damage on the tubular organ during and after placement in tubular organ, evenness of expansion and fineness of design allowing uniform coverage of the tubular organ, and non-X ray permeability allowing the surgeon to identify the desired location during catheter placement operation by X ray monitoring. For the purpose of satisfying these requirements, various stent designs were proposed, as disclosed, for example, in Patent Documents 1 and 2.

Recently, these stents are used more frequently in angioplasty of heart and carotid artery, and, although it was shown that placement of such a stent was effective in reducing the frequency of restenosis statistically significantly, the frequency of restenosis still remains high even now. For example in the case of cardiac coronary artery, it was reported that stent placement resulted in restenosis at a frequency of approximately 20 to 30%. Restenosis is induced both by biological vascular damage and also by vascular damage due to stent placement. Typical vascular constriction-restenosis induced by vascular damage is considered to be caused by proliferation of the intimal smooth muscle cells. First, the vascular damage induces proliferation of the smooth muscle cells, and the proliferated smooth muscle cells migrate into the inner membrane. Subsequently, the smooth muscle cells in the inner membrane proliferate with substrate deposition, thickening the inner membrane.

For example, Patent Document 3 proposes application of an obstruction-preventing drug on stent for reduction of restenosis rate. Examples of the obstruction-preventing drugs discussed include anticoagulant agents, antiplatelet agents, anticonvulsant agents, antibacterial agents, anti-tumor drugs, antimicrobial agents, antiinflammatory agents, anti-metabolism agents, immunosuppressive agents, and the like. Also proposed was a method of reducing restenosis by coating on stent an immunosuppressive agent, such as cyclosporine, tacrolimus (FK-506), Sirolimus (rapamycin), mycophenolate mofetil, or the analogue thereof. Specifically for example, Patent Document 4 discloses a stent coated with an immunosuppressive agent Sirolimus (rapamycin), while, for example, Patent Document 5 discloses a stent coated with an anti-tumor drug taxol (paclitaxel). For example, Patent Documents 6 and 7 disclose stents coated with tacrolimus (FK-506). However, there is currently, still restenosis after stent placement occurring at a certain rate even when such a medicine-coated stent is used, and there is a need for optimization of the basic stent design for further reduction of the restenosis rate.

A property demanded for the stent is favorable evenness of expansion. A stent should always expand evenly and disperse and withstand the force from the body internal lumen. When a stent is expanded unevenly, local concentration of the load may cause problems such as breakage or fracture of the stent and damage of body organs caused by uneven contact therewith. These problems may exert a great influence on restenosis after stent placement. In the case of a drug-coated stent, it is important to make the stent release the drug evenly into the body, and thus, the uniformity in expansion of stent is even more important.

Normally, a stent is designed to have multiple repeated basic units and in this way to be expanded evenly. However, during actual use, the stent is often expanded unevenly, because of the bent of the body internal lumen site where the stent is placed, and thus, there is currently a need for a stent design allowing uniform expansion of the stent even at the bent site.

Also demanded for the stent is favorable flexibility. The stent is often left in a narrow bent blood vessel, and the flexibility of the stent is particularly important in such a case. When the stent is less flexible, large force is consistently applied thereto, for example, by heart beat in the vascular region of stent placement. Alternatively when the stent is flexible, it is possible to reduce the stimulus to the blood vessel to the lowest level. However, there is a limit in improving flexibility by reducing the number of links in the axial direction or by thinning the links. Reduction in the number of links leads to deterioration in uniformity in expanding the stent, while thinning of the links to increased concern about breakdown by metal fatigue and breakage of the link region.

Patent Document 1: Japanese Unexamined Patent Publication No. 2-174859

Patent Document 2: Japanese Unexamined Patent Publication No. 6-181993

Patent Document 3: Japanese Unexamined Patent Publication No. 5-502179

Patent Document 4: Japanese Unexamined Patent Publication No. 6-9390

Patent Document 5: Japanese Unexamined Patent Publication No. 9-503488

Patent Document 6: WO 02/065947

Patent Document 7: EP Patent No. 1254674

DISCLOSURE OF THE INVENTION

Problems to be Solved by the Invention

An object of the present invention, which was made under the circumstances above, is to provide a stent for placement in body favorably expandable uniformly even in the bent region of an internal lumen and a stent for placement in body giving a low restenosis rate after placement.

Means to Solve the Problems

The inventors have found that it was important to provide some regions of the stent in the axial direction with a needed flexibility and that with flexibility varied in the axial direction, regions separated by a certain distance from the stent ends were the regions to be made most flexible.

The present invention has the following one or more aspects.

(1) A first aspect of the present invention is a stent for placement in body, characterized in that: the stent is a long tube-shaped body having both end regions; the long tube-shaped body is expandable in the radial direction from a compressed first diameter to a second expanded diameter; the stent has a first end section, a second end section, a third central section, a fourth section between the first end and the third central sections, and a fifth section between the second end and third central sections; the rigidity of the fourth section is smaller than that of the first end section and that of the third central section; and the rigidity of the fifth section is smaller than that of the second end section and that of the third central section.

(2) Another aspect of the present invention is a stent for placement in body, characterized in that: the stent is a long tube-shaped body having both end regions; the long tube-shaped body is expandable in the radial direction from a compressed first diameter to a second expanded diameter; the stent has a first end section, a second end section, a third central section, a fourth section between the first end and the third central sections, and a fifth section between the second end and third central sections; the cross sectional area of the basic shape strut in the fourth section is smaller than that of the basic shape strut in the first end section and that of the basic shape strut in the third central section; and the cross sectional area of the basic shape strut in the fifth section is smaller than that of the basic shape strut in the second end section and that of the basic shape strut in the third central section.

(3) Yet another aspect of the present invention is a stent for placement in body, characterized in that: the stent is long tube-shaped body flexible in the longitudinal direction for placement in body, having both end regions and multiple cylindrical shape elements; the cylindrical shape elements are formed with almost wave-formed elements; the cylindrical shape elements are expandable independently in the radial direction and connected to each other substantially in a well-aligned manner about the common axis line of the longitudinal direction; the long tube-shaped body is expandable in the radial direction from a compressed first diameter to a second expanded diameter; the stent has a first end section, a second end section, a third central section, a fourth section between the first end and the third central sections, and a fifth section between the second end and third central sections; the number of the almost wave-formed elements per circle in the fourth section is smaller than that in the first end section and that in the third central section; and the number of the almost wave-formed elements per circle in the fifth section is smaller than that in the second end section and that in the third central section.

(4) In the stent in a favorable embodiment thereof, the cross sectional area of the basic shape strut in the fourth section is smaller than that of the basic shape strut in the first end section and that of the basic shape strut in the third central section; and the cross sectional area of the basic shape strut in the fifth section is smaller than that of the basic shape strut in the second end section and that of the basic shape strut in the third central section.

The aspects (1) to (4) may be worked in combination of part or all of them. The characteristics and the advantageous effects of the present invention including those described above will be more obvious, when the invention is described with reference to the following embodiments and drawings.

Advantageous Effects of the Invention

According to the present invention, it is possible to expand a stent more uniformly than before, both in the straight and bent regions of internal lumen. Accordingly, the present invention provides a stent hardly causing restenosis after placement.

EXPLANATION OF REFERENCES

Figure 1:
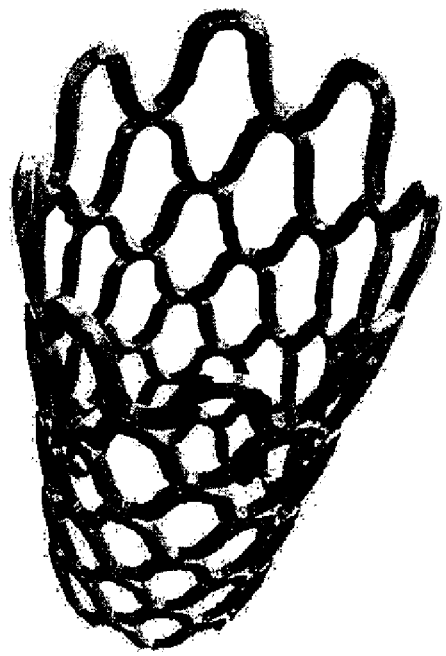
FIG. 1 is a schematic view showing a commonly-known stent for placement in body.

31 First end section
32 Second end section
33 Third central section
34 Fourth section
35 Fifth section
41 First end section
42 Second end section
43 Third central section
44 Fourth section
45 Fifth section 51 First end section
52 Second end section
53 Third central section
54 Fourth section
55 Fifth section

BEST MODE OF CARRYING OUT THE INVENTION

Hereinafter, favorable examples of the stent according to the present invention will be described, but the invention is not restricted by these examples.

1. Basic Shape

Figure 4:
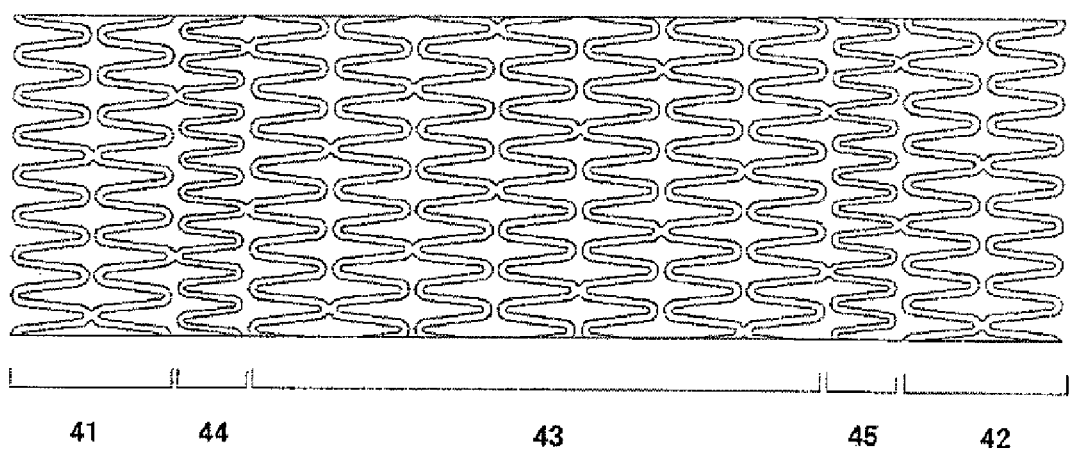
FIG. 4 is a development view showing the stent described in Example 2.

A development view of the stent for placement in body in an embodiment of the present invention is shown in FIG. 4. As is evident from FIG. 1, in the development views the axial direction of the stent is horizontal and the circumferential direction of the stent is vertical. The stent in FIG. 4 corresponds to the stent described in Example 1 below. The stents in FIGS. 5 and 6 also correspond to those in similar Examples: Hereinafter, only the embodiment shown in FIG. 4 will be described in detail for convenience of description.

The stent shown in FIG. 4 is characterized in that the stent is a long tube-shaped body having terminal ends; the long tube-shaped body is expandable in the radial direction from a compressed first diameter to a second expanded diameter; the net has a first end section 41, a second end section 42, a third central section 43, a fourth section 44 between the first end section 41 and the third central section 43, and a fifth section 45 between the second end section 42 and the third central section 43; the rigidity of the fourth section 44 is smaller than that of the first end section 41 and that of the third central section 43; and the rigidity of the fifth section 45 is smaller than that of the second end section 42 and that of the third central section 43.

In the present invention, as shown in FIG. 4, difference in the basic shape of each stent section leads to change in the rigidity of the stent section. The different basic shape is a concept, for example, including the case where the shape is different and also the cases where there is difference in width or thickness even if the shape is the same and thus there are substantially different physical properties.

2. Rigidity of Section

The rigidity of the first end section 41, second end section 42, third central section 43, fourth section 44, and fifth section 45 exemplified in FIG. 4 is the rigidity against the compression applied to the tube-shaped body in the radial direction. For comparison of the rigidities of respective sections, for example, the regions for respective sections are separated, and the compression strength in the radial direction is determined and converted to the compression strength per unit length of the tube-shaped body. It is possible to compare the rigidities of respective sections by using the compression strength per unit length. More specifically, each section of a stent is separated, for example, by physically cutting the stent with laser or with a sharp blade. The "rigidity of the section (e.g., compression strength per unit length)" is a value obtained by dividing the load applied, when a tube having a certain length (each stent section) is compressed by two parallel plates, for example, by 30% in the radial direction, by the length of each section. The compression strength can be measured generally by using an Autograph.

In an embodiment of the present invention, the fourth section 44 is more flexible to bending force than the first end section 41 and third central section 43, and the fifth section 45 to the second end section 42 and third central section 43.

When application of a bending force to the stent axial direction is assumed, the configuration highly flexible to bending force is a state in which a certain degree of bending is obtained with smaller bending force. Specifically, it means that the position first bent or having the largest bending deformation is the fourth section 44 (fifth section 45) when certain displacement is given to the central stent region while both stent ends are held still.

It is accomplished, for example, by a method of varying the basic shape constituting each section or by a method of varying the width and/or the thickness of the elements for the stent while preserving almost the same sectional shape. Alternatively, it is also possible by the connecting regions formed between the fourth section 44 and the third central section 43 and between the fifth terminal section 42 and the third central section 43 more flexible to bending force than other connecting regions, even when the basic shape of each section is kept the same and also the width and the thickness of the component are kept the same.

For comparison of rigidities to bending force of respective sections, two terminals of the section to be tested is held, as one of it is fixed and the other applied with a load. The flexural rigidity is determined by the load and the deformation. Then, it is necessary to keep the distance between the two holding positions constant.

3. Shape of Each Section

The first end section 41, the second end section 42, the third central section 43, the fourth section 44, and the fifth section 45 may have various shapes. For example, respective sections may be formed in combination of wave-shaped elements and connected to each other, forming a cylindrical tube. The shapes constituting the sections may be the same as or different from each other in design. The configuration of the present invention can be obtained by a method of changing the widths and/or the thicknesses of the elements constituting respective sections from each other.

The term "wave-formed" means that the shape is close to the shape of common sine wave, and also includes waveforms such as square, triangular, and saw-shaped forms. All wave-formed bents included in the wave-formed elements may have an identical waveform or multiple waveforms different in amplitude, width, or shape.

4. Stent-Producing Method

The stent-producing method for use may be any one of stent-producing methods commonly practiced such as laser processing, electric-discharge machining, mechanical machining, and etching. Surface smoothening of the strut end regions, by various polishing methods such as electropolishing, after stent production is well known in the art, and such a method is also applicable in the present invention.

The first diameter of the compressed stent is set to, for example, 1.2 mm or less, preferably 0.9 mm or less. The second diameter of the expanded stent, which is determined according to the internal diameter of the patient lumen, varies, depending on the lumen to be treatment. For example in the case of cardiac coronary artery, the second diameter is set to approximately 2.0 mm to 5.0 mm.

The stent length depends on the length of the area of the patient lumen to be treated. For example in the case of vascular system, a stent having a diameter of approximately 7 mm to 100 mm is used, while in the case of cardiac coronary artery, a stent having a diameter of approximately 7 to 40 mm is used.

5. Length and Location of Sections

The length of the first end section 41, the second end section 42, the third central section 43, the fourth section 44 and the fifth section 45 respectively in the axial direction is determined arbitrarily, but the fourth section 44 and the fifth section 45 are preferably located approximately a certain distance from the stent ends, independently of the total stent length. The fourth section 44 and the fifth section 45 are located in the area including the regions of approximately 1.35 mm to 3.75 mm separated from the stent ends, most preferably including the regions of approximately 2.70 to 3.55 mm. The fourth and fifth sections are preferably designed to have a length of approximately 1.0 mm to 3.0 mm, most preferable a length of approximately 1.0 mm to 1.5 mm, in the stent axial direction.

The advantageous effects of the stent being expanded uniformly as in the embodiment above are obtained when the location and/or the length of the fourth section 44 and the fifth section 45 are set respectively as described above. Specifically, during expansion, the deflection of the both ends of the stent (i.e., the first end section 41 and the second end section 42) when liberated from the first compressed state are seemingly absorbed and dispersed by the fourth section 44 and the fifth section 45 when liberated from the compressed state, preventing as a whole uneven expansion of the stent. The location and the length of the section absorbing and dispersing such deflection that may occur in the entire stent by expansion are determined, based on the idea of the inventors.

6. Examples of Stent Design

The stent in an embodiment of the present invention has the first end section 41, the second end section 42, the third central section 43, the fourth section 44 and the fifth section 45 respectively made of wave-shaped elements. The number of the wave-formed bents in the wave-shaped elements of the first end, second end, and third central sections, and that in the wave-shaped elements of the fourth and fifth sections may be different from each other. For example, the number of the wave-formed bents in the wave-shaped element constituting the first end, second end and third central sections may be 6 to 10, particularly approximately 8, and that in the wave-shaped elements constituting the fourth and fifth sections, 8 to 12, particularly approximately 10, and a wave-shaped element having approximately 10 waves may be narrower and thinner than that having approximately eight waves per circle.

In another embodiment, the wave-shaped element constituting the first end section 41, the second end section 42 and the third central section 43 may have a wave-formed bent number of 4 to 8, particularly approximately 6, per circle and that for the fourth section 44 and the fifth section 45, a wave-formed bent number of 6 to 10, particularly approximately 8, per circle. A wave-shaped element having approximately eight wave-formed bents per circle may be made narrower and thinner than that having approximately 6 wave-formed bents per circle.

The fourth and fifth sections should be made of an element more flexible than the first end, second end, and third central sections, and, for that purpose, the wave number of the fourth section and fifth sections may be increased, or the width of the strut constituting the fourth and fifth sections may be made narrower.

The phrase that the rigidity X1 of the fourth section (fifth section) is smaller than the rigidity Y1 of the first end section (the second end section) and the third central section means, for example, that the rigidity X1 is at most 99% or less, 95% or less, 90% or less, 80% or less, or 70% or less of the rigidity Y1 and at lowest 20% or more, 30% or more, 40% or more, 50% or more, or 60% or more.

The phrase that the cross sectional area X2 of the strut in the basic shape of the fourth section (fifth section) is smaller than the cross sectional area Y2 of the strut in the basic shapes of the first end section (second end section) and the third central section respectively means, for example, that the cross sectional area X2 is at most 99% or less, 95% or less, 90% or less, 80% or less, or 70% or less and at the lowest 20% or more, 30% or more, 40% or more, 50% or more, or 60% or more of the cross sectional area Y2.

The phrase that the wave number X3 per circle of the wave-shaped element of the fourth section (fifth section) is smaller than those Y3 per circle of the wave-shaped element of the first end section (the second end section) and the third central section respectively means, for example, that the difference between the wave number X3 and the wave number Y3 is at most 20 or less, 15 or less, 10 or less, 8 or less, or 5 or less and at lowest 1 or more, 2 or more, 3 or more, 4 or more, or 5 or more.

7. Structural Material

Metal materials favorable for the structural material include stainless steel, titanium, nickel, iridium, oxidation iridium magnesium, niobium, platinum, tantalum, gold, and the alloys thereof, as well as gold-plated iron alloys, platinum-plated iron alloys, cobalt chromium alloys, and titanium nitride-coated stainless steel. Favorably from the viewpoints of favorable rigidity and elasticity, the stent according to the present invention is made of a metal such as stainless steel, a nickel alloy such as Ni—Ti alloy, a Cu—Al—Mn alloy, or a Co—Cr alloy, or a combination thereof, and, for example, the metals specified in JIS-G4303 or the metals specified in ISO5832-5, ISO5832-6, and ISO5832-7 can also be used.

EXAMPLES

Hereinafter, favorable examples of the stent according to the present invention will be described with reference to drawings, but it should be understood that the present invention is not restricted thereby.

An example of the method of placing a stent is to fix the stent as it is compressed into the balloon region at the distal end of a catheter, feed the catheter and the stent into the patient lumen to be treated, fix the stent by expanding the balloon, and then, withdraw the catheter. Thus, the stent has two states: compressed state and expanded state. The stent is delivered in the compressed state and placed in a patient lumen in the expanded state. The stents in Comparative Examples and Examples shown below were prepared by a production method known in the art, i.e., by cutting a raw cylindrical metal tube into the shape of stent by laser cutting and additionally polishing the surface electrolytically.

Comparative Example 1

FIG. 1 is a schematic view of a commonly-known stent for placement in body, as seen from an inclined direction. The stent for placement in body shown in FIG. 1 is a long tube-shaped body having two end regions and cells of multiple wave-formed bents that are aligned to form an almost cylindrical tube between the end regions.

Figure 2:
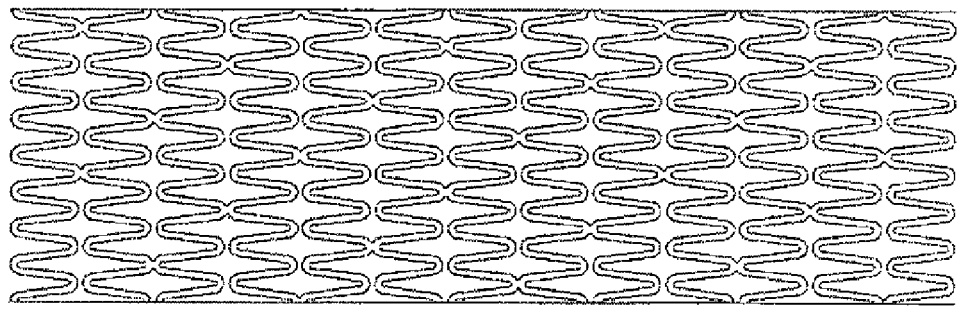
FIG. 2 is a development view showing a stent for placement in body corresponding to that described in Comparative Example 1.

FIG. 2 is a development view showing a structure of the long tube-shaped body of a typical stent for placement in body having two end regions corresponding to Comparative Example 1. The stent of Comparative Example 1 has multiple cylindrical shape elements; each of the cylindrical shape elements consists of almost wave-formed elements; these cylindrical shape elements are expandable in the radial direction; and the cylindrical shape elements are connected to each other substantially in a well-aligned manner about the common longitudinal-direction axis line by connecting some of the wave-top regions of the almost wave-formed elements each other. All cylindrical shape elements are the same-shaped elements that are connected to each other in the longitudinal direction axis line.

The strut in any region of the stent had a width of 130 μm, a thickness of 75 μm, a stent length of 17.45 mm, a stent external diameter 1.80 mm when prepared, and was prepared with the metal specified by 1805832-7. Each sections prepared had a wave number of 8 per circle.

Example 1

Figure 3:
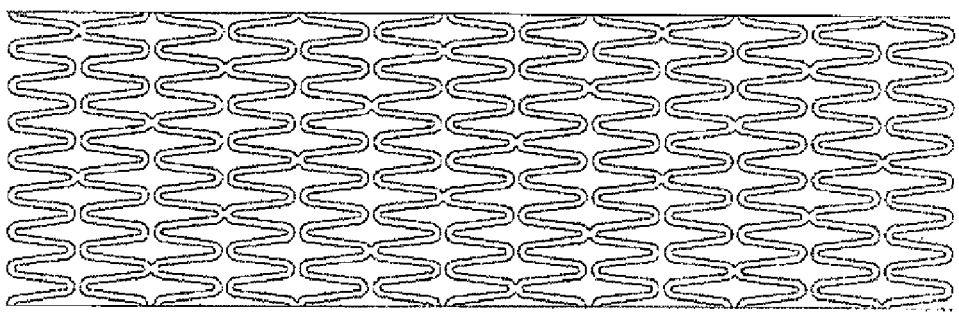
FIG. 3 is a development view showing the stent described in Example 1.

FIG. 3 is a development view showing a structure of the long tube-shaped body having both end regions of the stent for placement in body in an embodiment of the present invention. The stent of Example 1 has multiple cylindrical shape elements; each of the cylindrical shape elements consists of almost wave-formed elements; these cylindrical shape elements are expandable in the radial direction; and the cylindrical shape elements are connected to each other substantially in a well-aligned manner about the common longitudinal-direction axis line by connecting some of the wave-top regions of the almost wave-formed elements each other. The wave-shaped elements in the first end section 31, the second end section 32 and the third central section 33 respectively prepared had a strut having a width of 130 μm and a thickness of 75 μm, while the strut in the fourth section 34 and the fifth section 35 had a width of 110 μm, a thickness of 75 μm, and the stent having a stent length of 17.45 mm and a stent external diameter 1.80 mm after preparation was prepared. All of the first end section 31, the second end section 32, the third central section 33, the fourth section 34, and the fifth section 35 prepared had a wave number of 8 per circle. The raw material used for preparation of the metal was the metal specified by ISO5832-7. In Example 1, the fourth section 34 and the fifth section 35 were located at positions respectively 2.65 mm to 4.00 mm separated from the stent ends.

Example 2

FIG. 4 is a development view showing a structure of the long tube-shaped body having both end regions of the stent for placement in body in an embodiment of the present invention. The stent of Example 2 has multiple cylindrical shape elements; each of the cylindrical shape elements consists of almost wave-formed elements; these cylindrical shape elements are expandable in the radial direction; and the cylindrical shape elements are connected to each other substantially in a well-aligned manner about the common longitudinal-direction axis line by connecting some of the wave-top regions of the almost wave-formed elements each other.

As shown in FIG. 4, the cylindrical shape elements in the first end section 41, the second end section 42 and the third central section 43 have eight wave-formed bents per circle, while those in the fourth section 44 and the fifth section 45, ten wave-formed bents per circle. These cylindrical shape elements are connected to each other in the longitudinal direction axis line.

The wave-shaped elements in the first end section 41, the second end section 42 and third central section 43 respectively were made with a strut having a width of 130 μm, a thickness of 75 μm, while those in the fourth section 44 and the fifth section 45 were made with a strut having a width of 110 μm, a thickness of 75 μm, and the stent having a stent length of 18.40 mm and a stent external diameter 1.80 mm after preparation was prepared with the metal specified by ISO5832-7. The fourth section 44 and the fifth section 45 were located at positions respectively 2.70 mm to 3.75 mm separated from the stent ends.

Example 3

Figure 5:
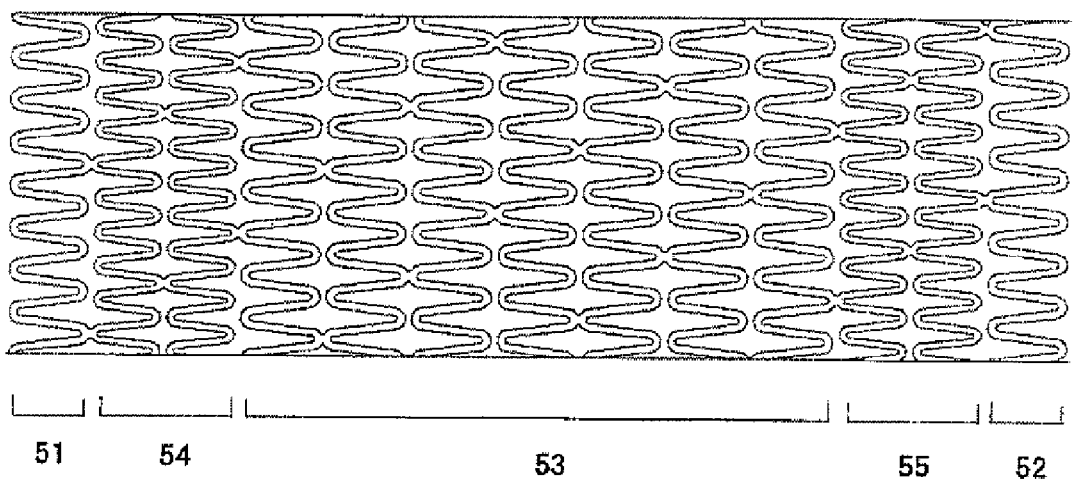
FIG. 5 is a development view showing the stent described in Example 3.

FIG. 5 is a development view showing a structure of the long tube-shaped body having both end regions of the stent for placement in body in an embodiment of the present invention. The stent of Example 3 has multiple cylindrical shape elements; each of the cylindrical shape elements consists of almost wave-formed elements; these cylindrical shape elements are expandable in the radial direction; and the cylindrical shape elements are connected to each other substantially in a well-aligned manner about the common longitudinal-direction axis line by connecting some of the wave-top regions of the almost wave-formed elements each other.

As shown in FIG. 5, the cylindrical shape elements in the first end section 51, the second end section 52 and the third central section 53 have eight wave-formed bents per circle, while those in the fourth section 54 and the fifth section 55, ten wave-formed bents per circle. These cylindrical shape elements are connected to each other in the longitudinal direction axis line. The wave-shaped elements in the first end section 51, the second end section 52 and third central section 53 respectively were made with a strut having a width of 130 μm, a thickness of 75 μm, while those in the fourth section 54 and the fifth section 55 were made with a strut having a width of 110 μm, a thickness of 75 μm, and the stent having a stent length of 18.00 mm and a stent external diameter 1.80 mm after preparation was prepared with the metal specified by ISO5832-7. The fourth section 54 and the fifth section 55 were located at positions respectively 1.35 mm to 3.55 mm separated from the stent ends.

Example 4

Figure 6:
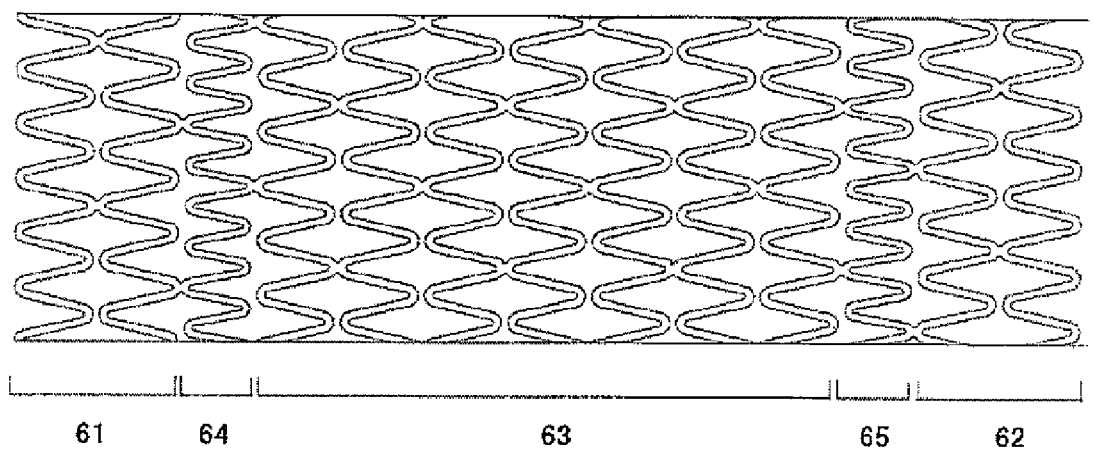
FIG. 6 is a development view showing the stent described in Example 4.

FIG. 6 is a development view showing a structure of the long tube-shaped body having both end regions of the stent for placement in body in an embodiment of the present invention. The stent of Example 4 has multiple cylindrical shape elements; each of the cylindrical shape elements consists of almost wave-formed elements; these cylindrical shape elements are expandable in the radial direction; and the cylindrical shape elements are connected to each other substantially in a well-aligned manner about the common longitudinal-direction axis line by connecting some of the wave-top regions of the almost wave-formed elements each other.

As shown in FIG. 6, the cylindrical shape elements in the first end section 61, the second end section 62, and the third central section 63 have six wave-formed bents per circle, while those in the fourth section 64 and the fifth section 65, eight wave-formed bents per circle. These cylindrical shape elements are connected to each other in the longitudinal direction axis line. The wave-shaped elements in the first end section 61, the second end section 62, and the third central section 63 respectively were made with a strut having a width of 130 μm, a thickness of 75 μm, while those in the fourth section 64 and the fifth section 65 were made with a strut having a width of 110 μm, a thickness of 75 μm, and the stent having a stent length of 18.40 mm and a stent external diameter 1.80 mm after preparation was prepared with the metal specified by ISO5832-7. The fourth section 44 and the fifth section 45 were located at positions respectively 2.70 mm to 3.75 mm separated from the stent ends.

(Evaluation)

The stents obtained in Comparative Example 1 and Examples 1 to 4 above were subjected to the following evaluation test.

First, each of the stents for evaluation is compressed and fixed into the balloon region of a balloon catheter. The balloon catheter used then was a rapid exchange balloon catheter having a balloon diameter of 3.0 mm and a balloon region length of 20 mm at the rated expansion pressure. Separately, a silicone artificial blood vessel having an internal diameter of 3.0 mm and an external diameter of 4.0 mm was made available.

The artificial blood vessel was placed in the linear straight state, and each stent was placed as expanded in the artificial blood vessel. The stent placement was carried out by expanding the balloon at a pressure of 8 atm and leaving the stent expanded for 30 seconds, depressuring the balloon, and then withdrawing the balloon out of the artificial blood vessel. Then, the twist of the stent left in the artificial blood vessel was evaluated. The evaluation was made by observing the twist angle between the stent ends, and the measured value was obtained relative to the twist angle corresponding to full circle of 360 degrees. It was expressed as an absolute value, without consideration of the twist direction. Three samples were measured in each test group, and the average twist angles in respective groups are summarized in the following Table 1.

TABLE 1

|  | Average twist angle |
| --- | --- |
| Comparative Example 1 | 6.7% |
| Example 1 | 5.6% |
| Example 2 | 2.3% |
| Example 3 | 3.7% |
| Example 4 | 2.2% |

The results showed that the twist angle was smaller in any Example than in Comparative Example. The twist angle in Example 1, which was the largest in all Examples, was 5.6%, i.e., 1.1% smaller than that in Comparative Example 1, which was equivalent to a relative reduction rate in twist angle of approximately 16% from that in Comparative Example. Alternatively the twist angle in Example 4, with was the smallest in all Examples, was 2.2%, smaller by 4.5% than that in Comparative Example 1, that was equivalent to a relative reduction rate of approximately 67% from that in the Comparative Example.

Subsequently, the artificial blood vessel was placed as it was bent by an angle of 90 degrees. The bent region of the artificial blood vessel was such that the inward side of the periphery of the bent region had a curvature radius of 10 mm. Each stent was placed as expanded in the artificial blood vessel. The stent was placed in the center of the bent region of the artificial blood vessel. Similarly to the test above, the stent placement was carried out by expanding the balloon at a pressure of 8 atm and leaving the stent expanded for 30 seconds, depressuring the balloon, and then withdrawing the balloon out of the artificial blood vessel. Then, the twist of the stent left in the artificial blood vessel was evaluated. The evaluation was made by observing the twist angle between the stent ends, and the measured value was obtained relative to the twist angle corresponding to full circle of 360 degrees. It was expressed as an absolute value, without consideration of the twist direction. Three samples were measured in each test group, and the average twist angles in respective groups are summarized in the following Table 2.

TABLE 2

|  | Average twist angle |
| --- | --- |
| Comparative Example 1 | 12.1% |
| Example 1 | 9.2% |
| Example 2 | 6.2% |
| Example 3 | 8.3% |
| Example 4 | 5.5% |

The results showed that the twist angle was smaller in any Examples than in Comparative Example. The twist angle in Example 1, which was the largest in all Examples, was 9.2%, i.e., 2.9% smaller than that in Comparative Example 1, which was equivalent to a relative reduction rate in twist angle of approximately 24% from that in Comparative Example. Alternatively the twist angle in Example 4, which was the smallest in all Examples, was 5.5%, smaller by 6.6% than that in Comparative Example 1, which was equivalent to a relative reduction rate of approximately 55% from that in the Comparative Example.

The invention claimed is:

1. A stent for placement in a human body, characterized in that:
   the stent is a long tube-shaped body having both end regions;
   the long tube-shaped body is expandable in the radial direction from a compressed first diameter to a second expanded diameter;
   the stent has a first end section, a second end section, a third central section, a fourth section between the first end and the third central sections, and a fifth section between the second end and third central sections;
   each of the first through the fifth sections extends continuously around a circumferential direction of the stent and the first through the fifth sections connect to one another along an axial direction of the stent;
   a rigidity of the fourth section is smaller than that of the first end section and that of the third central section;
   a rigidity of the fifth section is smaller than that of the second end section and that of the third central section;
   each of the first through fifth sections are formed with almost wave-formed elements;
   a number of the almost wave-formed elements per circle in the fourth section is larger than that in the first end section and that in the third central section; and
   a number of the almost wave-formed elements per circle in the fifth section is larger than that in the second end section and that in the third central section.

2. A stent for placement in a human body according to claim 1, wherein the fourth section and the fifth section are located within a region that is between approximately 1.35 mm and 3.75 mm from the first end or the second end of the stent, respectively.

3. A stent for placement in a human body according to claim 1, wherein the fourth section and the fifth section are located within a region that is between approximately 1.35 mm and 3.75 mm from the first end or the second end of the stent, respectively.

4. A stent for placement in a human body according to claim 1, wherein the rigidity of the fourth section and of the fifth section is between 20% and 99% of the rigidity of any one of the first section, the second section, and the third section.

5. A stent for placement in a human body according to claim 1, wherein each of the first through the fifth sections is made of a wave-shaped element formed into a number of wave-formed bends.

6. A stent for placement in a human body, characterized in that:
   the stent is a long tube-shaped body having both end regions;
   the long tube-shaped body is expandable in the radial direction from a compressed first diameter to a second expanded diameter;
   the stent has a first end section, a second end section, a third central section, a fourth section between the first end and the third central sections, and a fifth section between the second end and third central sections;
   each of the first through the fifth sections extends continuously around a circumferential direction of the stent and the first through the fifth sections connect to one another along an axial direction of the stent;
   a cross sectional area of the basic shape strut in the fourth section is smaller than that of the basic shape strut in the first end section and that of the basic shape strut in the third central section;
   a cross sectional area of the basic shape strut in the fifth section is smaller than that of the basic shape strut in the second end section and that of the basic shape strut in the third central section;
   each of the first through fifth sections are formed with almost wave-formed elements;
   a number of the almost wave-formed elements per circle in the fourth section is larger than that in the first end section and that in the third central section; and
   a number of the almost wave-formed elements per circle in the fifth section is larger than that in the second end section and that in the third central section.

7. A stent for placement in a human body according to claim 6, wherein the fourth section and the fifth section are located within a region that is between approximately 1.35 mm and 3.75 mm from the first end or the second end of the stent, respectively.

8. A stent for placement in a human body according to claim 6, wherein the rigidity of the fourth section and of the fifth section is between 20% and 99% of the rigidity of any one of the first section, the second section, and the third section.

9. A stent for placement in a human body according to claim 6, wherein each of the first through the fifth sections is made of a wave-shaped element formed into a number of wave-formed bends, and
   wherein in each of the first through the fifth sections the basic shape strut comprises the wave-shaped element.

10. A stent for placement in a human body, characterized in that:
    the stent is long tube-shaped body flexible in the longitudinal direction for placement in body, having both end regions and multiple cylindrical shape elements;
    the cylindrical shape elements are formed with almost wave-formed elements;
    the cylindrical shape elements are expandable independently in the radial direction and connected to each other substantially in a well-aligned manner about the common axis line of the longitudinal direction;
    the long tube-shaped body is expandable in the radial direction from a compressed first diameter to a second expanded diameter;
    the stent has a first end section, a second end section, a third central section, a fourth section between the first end and the third central sections, and a fifth section between the second end and third central sections;
    each of the first through the fifth sections extends continuously around a circumferential direction of the stent and the first through the fifth sections connect to one another along an axial direction of the stent;
    the number of the almost wave-formed elements per circle in the fourth section is larger than that in the first end section and that in the third central section;
    the number of the almost wave-formed elements per circle in the fifth section is larger than that in the second end section and that in the third central section;
    a cross sectional area of the basic shape strut in the fourth section is smaller than that of the basic shape strut in the first end section and that of the basic shape strut in the third central section;
    a cross sectional area of the basic shape strut in the fifth section is smaller than that of the basic shape strut in the second end section and that of the basic shape strut in the third central section; and
    the rigidity of the fourth section and of the fifth section is between 20% and 99% of a rigidity of any one of the first section, the second section, and the third section.

11. A stent for placement in a human body according to claim 10, wherein the fourth section and the fifth section are located within a region that is between approximately 1.35 mm and 3.75 mm from the first end or the second end of the stent, respectively.

12. A stent for placement in a human body according to claim 10, wherein each of the first through the fifth sections is made of a wave-shaped element formed into a number of wave-formed bends.

* * * * *